United States Patent [19]

Manzer et al.

[11] Patent Number: 4,911,792

[45] Date of Patent: Mar. 27, 1990

[54] PROCESS FOR THE SEPARATION OF HF VIA PHASE SEPARATION AND DISTILLATION

[75] Inventors: Leo E. Manzer; V. N. Mallikarjuna Rao, both of Wilmington, Del.; Richard T. Rockwell; Michael A. Sisk, both of Corpus Christi, Tex.; Edwin J. Warwas, Wilmington; Roy Winteringham, Hockessin, both of Del.

[73] Assignee: E. I. Du Pont de Nemours and Company, Wilmington, Del.

[21] Appl. No.: 226,736

[22] Filed: Aug. 1, 1988

[51] Int. Cl.$^4$ .......................... B01D 3/10; C07C 25/00
[52] U.S. Cl. ......................................... 203/39; 203/78; 203/80; 570/178
[58] Field of Search .................. 203/75, 77, 78, 80, 203/39; 570/168, 178

[56] References Cited

U.S. PATENT DOCUMENTS

| | | | |
|---|---|---|---|
| 2,425,752 | 8/1947 | McKenna et al. | 203/39 |
| 2,450,414 | 10/1948 | Benning | 203/80 |
| 2,450,415 | 10/1948 | Benning | 203/80 |
| 2,478,362 | 8/1949 | Benning | 202/51 |
| 2,549,609 | 4/1951 | Johnson | 570/178 |
| 3,406,099 | 10/1968 | Buckman et al. | 203/50 |
| 3,873,629 | 3/1975 | Jones | 260/653 |
| 3,947,558 | 3/1976 | van Eijl | 423/483 |
| 3,976,447 | 8/1976 | Merchant et al. | 55/71 |
| 4,209,470 | 6/1980 | Lorquet | 260/652 P |
| 4,766,258 | 8/1988 | Komatsu | 570/168 |

FOREIGN PATENT DOCUMENTS 0098341 1/1984 European Pat. Off. .

Primary Examiner—Virginia Manoharan

[57] ABSTRACT

Process for the separation of HF, 2,2-dichloro-1,1,1-trifluoroethane (FC-123) and/or 2-chloro-1,1,1,2-tetrafluoroethane (FC-124) mixture by subjecting the mixture to a temperature from about −80° C. to about 40° C. and a pressure from about 0.10 MPa to about 3.55 MPa in a separation zone, whereby an organic phase having less than 15 mole percent of HF is formed as the bottom layer in the separation zone and an acid phase having at least 93 mole percent of HF is formed at the top in the separation zone.

6 Claims, 2 Drawing Sheets

PROCESS FOR THE SEPARATION OF HF VIA PHASE SEPARATION AND DISTILLATION

FIELD OF INVENTION

Process for the separation of mixtures comprising hydrogen fluoride (HF), 2,2-dichloro-1,1,1-trifluoroethane (FC-123), and/or 2-chloro-1,1,1,2-tetrafluoroethane (FC-124) by subjecting the mixture to phase separation.

BACKGROUND OF THE INVENTION

The efficient utilization of HF is important from both economic and process operability viewpoints. Techniques to effect the separation and recovery of HF from fluorocarbon process streams have been disclosed.

U.S. Pat. No. 2,478,362 dicloses the use of a continuous separation zone to separate an organic phase from HF and then recycling the latter to the reactor feed system.

U.S. Pat. No. 3,406,099 discloses an azeotropic system useful for separation of $CF_3COCF_3$, HF or $CCl_2FCClF_2$ from mixtures containing one or more of these materials.

U.S. Pat. No. 3,873,629 discloses a continuous process for separating mixtures of HF and $ClCHF_2$ by countercurrent contact of a gaseous mixture of the two components with $H_2SO_4$.

U.S. Pat. No. 3,947,558 discloses a process for the separation of HF from the reaction products generated by fluorinating a 1–3 carbon chlorinated hydrocarbon by first separating HCl, followed by cooling to form an HF-rich late and an HCl-free organic layer. This latter layer is mixed with a liquid 2 to 8 carbon glycol; after which an HF-enriched glycol layer is separated from the halocarbon layer. HF is recovered from the glycol by distillation.

U.S. Pat. No. 3,976,447 discloses the separation of HF from gaseous mixtures by treatment with dry particles of $CaCl_2$, $BaCl_2$, or $SrCl_2$, after which the HF is desorbed.

U.S. Pat. No. 4,209,470 discloses a process for the separation of HF from its liquid mixtures with 1-chloro-1,1-difluoroethane by adding an auxiliary solvent to enhance the HF composition of a liquid inorganic phase in a separation zone. The HF is then separated from the inorganic phase by distillation.

EP 98,341 discloses a process for the separation of HF and 1-chloro-1,1-difluoroethane which does not require an auxiliary solvent even through the feed stream to the separation zone contains pentafluorobutane which the disclosure states should contribute to the mutual solubility of HF and 1-chloro-1,1-difluoroethane; and therefore, should hinder a phase separation process. The separation is done without the use of auxiliary solvents by avoiding contamination and exercising good temperature control.

The need to produce alternate fluorocarbons useful as refrigerants and blowing agents or as intermediates in the production of other fluorocarbons useful as refrigerants and blowing agents has spurred an interest in processes for the preparation of FC-123 and FC-124. These are useful themselves as blowing agents, refrigerants and intermediates in the preparation of 1,1,1,2-tetrafluoroethane (FC-134a), a highly useful fluorocarbon refrigerant.

One process for the preparation of FC-123 and FC-124, described in commonly assigned application Ser. No. 070,826, filed July 7, 1987, involves vapor phase hydrofluorination of halogenated alkenes with excess HF. This process produces a reaction mixture effluent consisting essentially of HF, FC-123, FC-124, tetrachloroethylene, HCl and minor (less than 5 mole percent) amounts of other halogenated products, such as 1,2,2-trichloro-1,1-difluoroethane (FC-122) and pentafluoroethane (FC-125). Removal of HCl and FC-125 can be easily accomplished by simple distillation, leaving a mixture consisting of hydrogen fluoride (HF), FC-123, FC-124, tetrachloroethylene, and minor (e.g., less than 5 mol percent) amounts of other halogenated products. One method for separating the reaction mixture, described in Applicants concurrently filed application Ser. No. 226,737, utilizes the formation of HF azeotropes with FC-123 and FC-124 under conditions of controlled HF/FC-123 ratios.

The instant invention provides an alternate route to separation of HF from FC-123 and FC-124 utilizing phase separation and distillation.

SUMMARY OF THE INVENTION

The present invention provides a process for the separation of a mixture comprising hydrogen fluoride (HF), 2,2-dichloro-1,1,1-trifluoroethane (FC-123), and/or 2-chloro-1,1,1,2-tetrafluoroethane (FC-124) by condensing the mixture at a temperature from about $-80°$ C. to about 40° C. and a pressure from about 0.10 MPa to about 3.55 MPa in a separation zone, whereby an organic phase comprising less than 15 mole percent HF is formed as the bottom layer in the separation zone and an acid phase comprising at least 93 mole percent HF is formed as the top layer in the separation zone.

The organic phase, consisting essentially of at least 85 mole percent of at least one of FC-123, FC-124, other organic compounds which may be present, and less than 15 mole percent HF can be withdrawn from the bottom of the separation zone and subjected to distillation to remove any remaining HF. The distillate comprising HF can be recovered from the top of the distillation column and recycled to the separation zone, if desired, to recover additional HF. The acid phase, consisting essentially of at least 93 mole percent HF and less than 7 mole percent of at least one of FC-123, FC-124 and other organic compounds which may be present, can be withdrawn from the top of the separation zone and subjected to distillation to remove any remaining FC-123, FC-124 and other organic compounds which may be present. The distillate comprising HF can be recovered from the top of the distillation column and recycled to the separation zone, if desired, for reasons set forth above. Other organic compounds which may be present include tetrachloroethylene and minor (e.g., less than 5 mole percent) amounts of other halogenated products.

The invention provides for the substantially complete separation of HF from the organic components utilizing phase separation and distillation techniques. It capitalizes on the discovery that HF, FC-123 and FC-124 form azeotropes that are more volatile than their individual components. Further, it depends on the formation of these azeotropes in the distillative stripping of HF substantially completely from the organic phase and in the distillative stripping of the organic components substantially completely from the acid phase, thereby enabling the separate recovery of substantially pure HF and organic fractions.

The invention also takes advantage of the further discovery that the proportions of HF in the azeotropic compositions (recovered in the distillative stripping of the acid and the organic phases) are greater than exist in the liquid organic phase of the two-phase system formed on condensing the original feed mixture. Likewise the proportions of organics in the azeotropic compositions are greater than exist in the liquid acid phase of the two-phase system. Thus recycling the azeotropic compositions to the feed mixture condensation step results in an overall enhanced degree of separation and eventually complete separation of HF and the organics, one from the other.

DETAILS OF THE INVENTION

Figure 1:
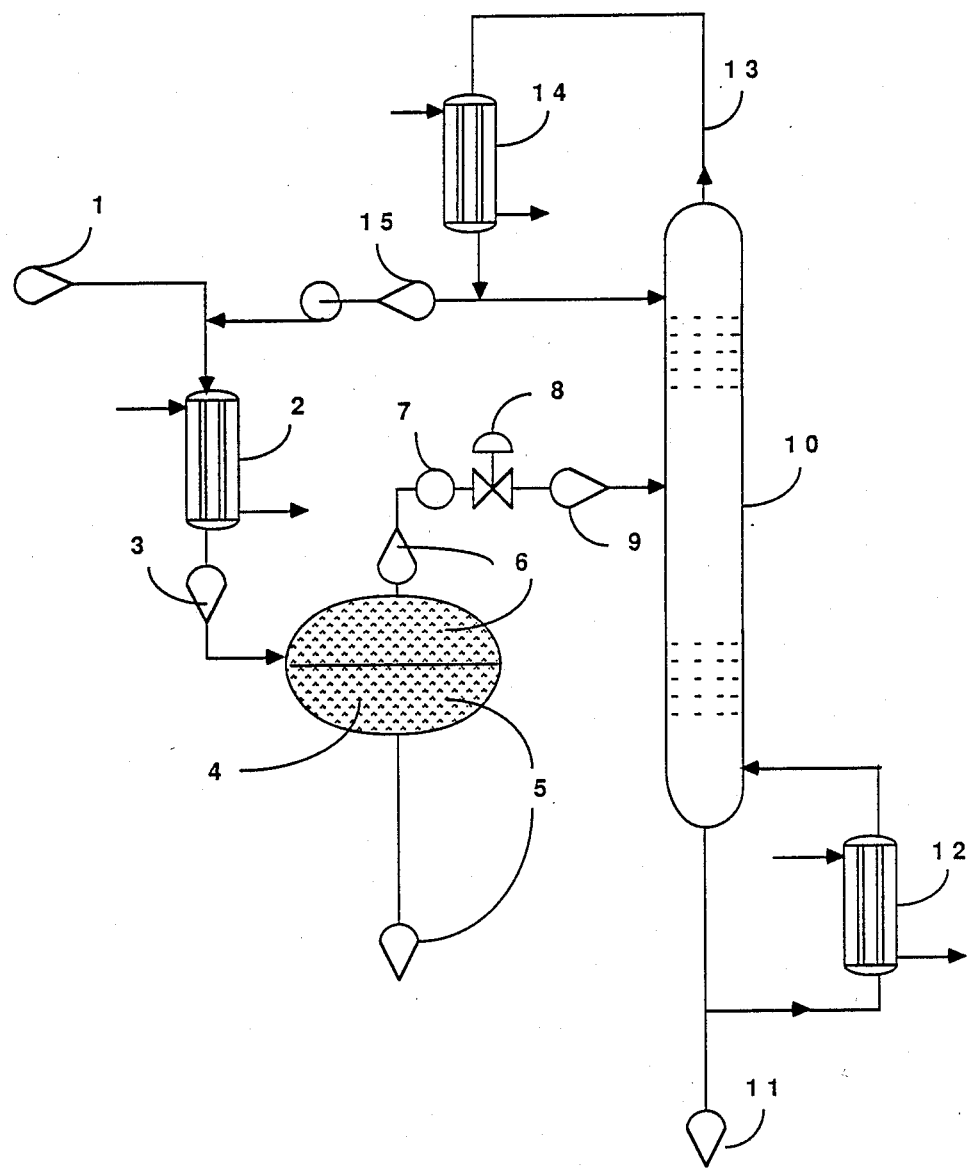
FIG. 1 is a schematic flow diagram of one embodiment of the process of the invention.

While the feed mixture treated in accordance with the instant invention can be obtained from a variety of sources, an advantageous use of the instant invention resides in treating the effluent mixture from the preparation of FC-123 and FC-124 by reaction of tetrachloroethylene with HF, so that products from the reaction can be withdrawn or recycled as desired. The effluent mixture from this reaction generally consists essentially of HF, FC-123, FC-124, tetrachloroethylene, HCl, and minor amounts of halogenated products, such as 1,2,2-trichloro-1,1-difluoroethane (FC-122) and pentafluoroethane (FC-125). Low boiling components, such as HCl and FC-125, can be conventionally removed, leaving a mixture consisting essentially of hydrogen fluoride (HF), FC-123, FC-124, tetrachloroethylene, and minor (less than 5 mol percent) amounts of other halogenated products, which can advantageously be treated in accordance with the instant invention.

Applicants have found that two phases are formed at a variety of temperatures and pressures. At atmospheric pressure and −40° C., HF and FC-123 form two phases: an acid phase, consisting essentially of 98.3 mole percent (88.5 weight percent) HF and 1.7 mole percent (11.5 weight percent) FC-123, and an organic phase consisting essentially of 98.6 mole percent (99.8 weight percent) FC-123 and 1.4 mole percent (0.2 weight percent) HF. At the same temperature and pressure HF and FC-124 also form two phases: an acid phase, consisting essentially of 84.9 mole percent (45.2 weight percent) HF and 15.1 mole percent (54.8 weight percent) FC-124, and an organic phase consisting essentially of 97.6 mole percent (99.6 weight percent) FC-124 and 2.4 mole percent (0.4 weight percent) HF.

Utilizing this information applicants discovered that subjecting mixtures, comprising HF, FC-123, FC-124, and optionally, other organic compounds, to a temperature from about −80° C. to 40° C., preferably from about −40° C. to about 0° C., and a pressure from about 0.10 MPa to about 3.55 MPa, preferably from about 0.10 MPa to about 1.83 MPa in a separation zone results in the formation of an organic phase comprising less than 15 mole percent HF and an acid phase comprising at least 93 mole percent of HF.

The organic phase forms at the bottom of the separation zone and consists essentially of less than 15 mole percent HF and at least 85 mole percent of at least one of FC-123, FC-124 and other organic compounds which may be present. The acid phase forms at the top of the separation zone and consists essentially of at least 93 mole percent HF and less than 7 mole percent of at least one of FC-123, FC-124 and other organic compounds which may be present. The exact amounts of the various components of the organic and acid phases within the ranges specified are dependent on the amounts of these components in the original mixture and the mutual solubilities of the phases at operating temperature and pressure.

Figure 2:
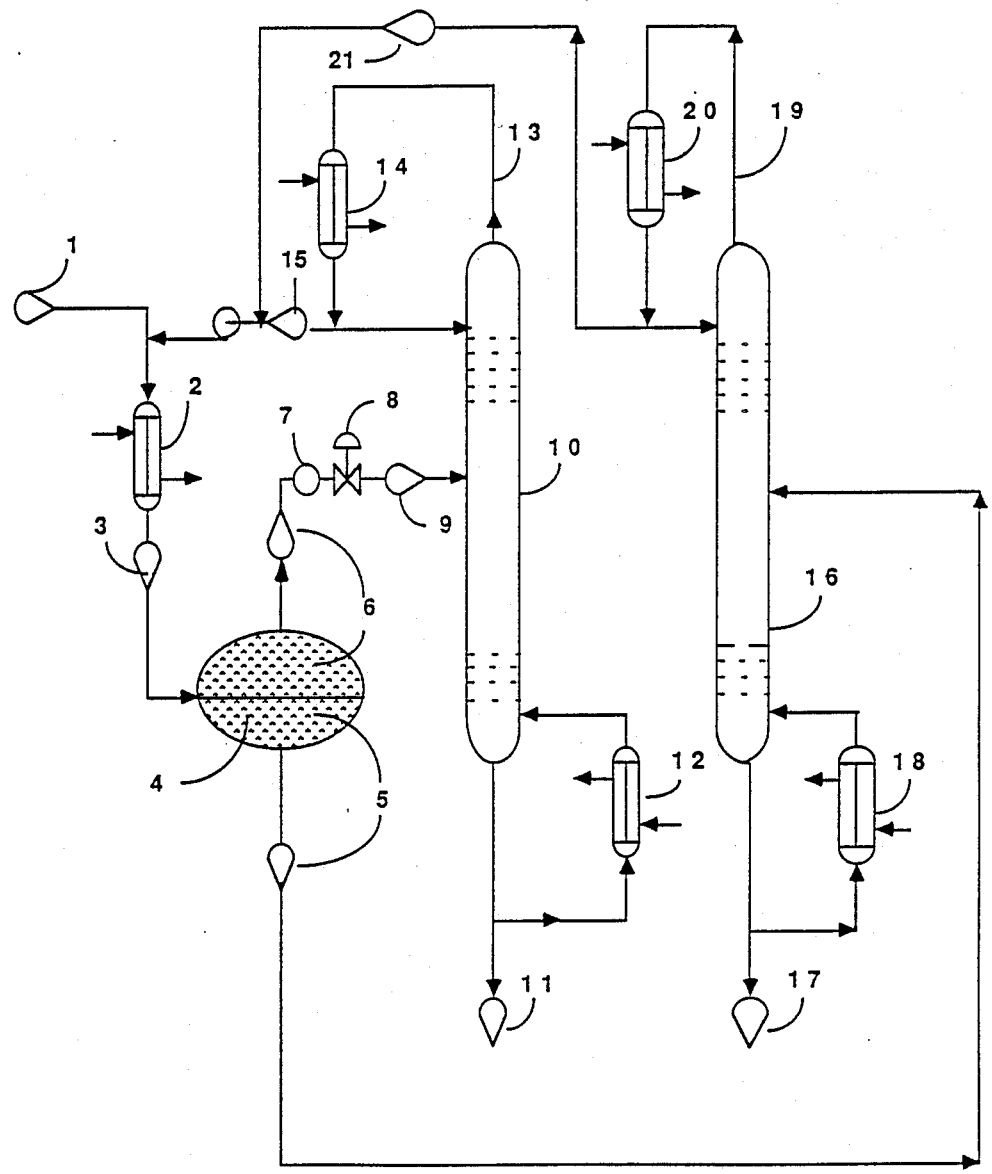
FIG. 2 is a schematic diagram of a second embodiment of the invention.

Preferred embodiments of the invention are illustrated by FIGS. 1 and 2. Referring to the figures, a mixture of 1 of FIG. 1 and FIG. 2 consisting essentially of HF, FC-123, FC-124 and minor amounts of other halogenated products is passed through a cooler 2 of FIG. 1 and FIG. 2 at a temperature from about −80° C. to about 40° C. and pressure from about 0.10 MPa to about 3.55 MPa, the cooled mixture 3 of FIG. 1 and FIG. 2 is sent to separation zone 4 of FIG. 1 and FIG. 2, maintained at a temperature from about −80° C. to 40° C. and pressure from about 0.10 MPa to about 3.55 MPa where an organic phase 5 of FIG. 1 and FIG. 2 containing less than 15 mol percent HF and an acid phase 6 of FIG. 1 and FIG. 2 containing at least 93 mol percent HF are formed. The acid phase 6 is removed from the top of the separation zone 4 and passed through heat exchanger 7 and pressure adjuster 8 of FIG. 1 and FIG. 2, and the resulting acid phase 9 of FIG. 1 and FIG. 2 is fed to a multiple-plate distillation column 10 of FIG. 1 and FIG. 2. The temperature at the top of column 10 is preferably from about −4° C. to about 133° C., and more preferably from about −4° C. to 97° C., and the pressure preferably from about 0.10 MPa to about 3.55 MPa, and more preferably from about 0.10 MPa to about 1.83 MPa, the exact temperature being dependent on the pressure. Essentially pure HF 11 of FIG. 1 and FIG. 2 can be removed from the bottom of column 10. Reboiler 12, of FIGS. 1 and 2, provides heat input to the column by revaporizing a portion of mixture 11. A mixture of HF, FC-123 and FC-124, as well as minor amounts of other halogenated products can be removed from the top 13, of the column 10 of FIG. 1 and FIG. 2, passed through a condenser 14 of FIG. 1 and FIG. 2. The resulting mixture 15 of FIG. 1 and FIG. 2 can then be recycled through cooler 2 to separation zone 4.

In a further embodiment the organic phase 5 can be sent to a second multiple-plate distillation column 16 of FIG. 2 having a temperature at the top of from about −15° C. to about 120° C., and a pressure from about 0.10 MPa to about 3.55 MPa, preferably about 0.69 MPa to about 1.83 MPa. A mixture of FC-123, FC-124 and other organic compounds which may be present, 17 of FIG. 2 can be removed from the bottom of column 16 or recycled through reboiler 18 of FIG. 2, to column 16. A mixture of FC-123 and FC-124 with HF, 19 of FIG. 2, can be removed from the top of column 16, cooled in condenser 20, and, passed directly, 21 of FIG. 2, to cooler 2 for recycle to the separation zone 4. Condenser 20 also provides reflux liquid for column 16.

EXAMPLES

In the following illustrative examples, all values for the compounds are in moles, temperatures are in Celsius. All the data were obtained by calculation using measured and calculated thermodynamic properties. The numbers at the top of the columns refer to FIG. 1 for Tables 1–8 and to FIG. 2 for Tables 9–14.

EXAMPLE 1

The purification system with a separation zone temperature of −40° C. and one multiple plate distillation column is being operated as shown in Table 1. The mole percent of HF in the acid phase is 97.4 and in the organic phase 1.5.

TABLE 1

| Compound | 1 Feed Mix. | 3 Decant Feed | 6 Acid Phase | 5 Organic Phase | 11 Pure HF | 15 Top Prod. | 9 Col. Feed |
|---|---|---|---|---|---|---|---|
| HF | 53.84 | 55.10 | 54.38 | 0.72 | 53.11 | 1.26 | 54.37 |
| FC-123 | 38.30 | 39.30 | 1.00 | 38.30 | 0.00 | 1.00 | 1.00 |
| FC-124 | 7.79 | 8.23 | 0.44 | 7.79 | 0.00 | 0.44 | 0.44 |
| Temp °C. | 101 | −40 | −40 | −40 | 20 | −3 | 0 |
| Press. MPa | 1.83 | 1.83 | 1.83 | 1.83 | 0.10 | 0.10 | 0.10 |

EXAMPLE 2

The effect of varying the temperature of the separation zone is shown in Tables 2, 3, 4 and 5.

TABLE 2

| Compound | 3 Decant Feed | 6 Acid Phase | 5 Organic Phase |
|---|---|---|---|
| HF | 53.65 | 46.49 | 7.16 |
| FC-123 | 38.27 | 2.09 | 36.18 |
| FC-124 | 8.00 | 0.76 | 7.24 |
| Mole % HF |  | 94.2 | 14.2 |
| Temp °C. | 40 | 40 | 40 |
| Press. MPa | 1.83 | 1.83 | 1.83 |

TABLE 3

| Compound | 3 Decant Feed | 6 Acid Phase | 5 Organic Phase |
|---|---|---|---|
| HF | 53.64 | 51.31 | 2.33 |
| FC-123 | 38.27 | 1.47 | 36.80 |
| FC-124 | 8.00 | 0.59 | 7.41 |
| Mole % HF |  | 96.1 | 5.0 |
| Temp °C. | 0 | 0 | 0 |
| Press. MPa | 1.83 | 1.83 | 1.83 |

TABLE 4

| Compound | 3 Decant Feed | 6 Acid Phase | 5 Organic Phase |
|---|---|---|---|
| HF | 53.64 | 52.94 | 0.70 |
| FC-123 | 38.27 | 0.98 | 37.29 |
| FC-124 | 8.00 | 0.42 | 7.58 |
| Mole % HF |  | 97.4 | 1.5 |
| Temp °C. | −40 | −40 | −40 |
| Press. MPa | 1.83 | 1.83 | 1.83 |

TABLE 5

| Compound | 3. Decant Feed | 6 Acid Phase | 5 Organic Phase |
|---|---|---|---|
| HF | 53.65 | 53.46 | 0.19 |
| FC-123 | 38.27 | 0.56 | 37.71 |
| FC-124 | 8.00 | 0.27 | 7.73 |
| Mole % HF |  | 98.5 | 0.4 |
| Temp °C. | −80 | −80 | −80 |
| Press. MPa | 1.83 | 1.83 | 1.83 |

EXAMPLE 3

The effect of operating the distillation column at different pressures and temperatures is shown in Tables 6–8.

TABLE 6

| Compound | 11 Pure HF | 15 Top Product | 9 Column Feed |
|---|---|---|---|
| HF | 93.51 | 3.89 | 97.40 |
| FC-123 |  | 1.80 | 1.80 |
| FC-124 |  | 0.78 | 0.78 |
| Temp °C. | 20 | −4 | 0 |
| Press. MPa | 0.10 | 0.10 | 0.10 |

TABLE 7

| Compound | 11 Pure HF | 15 Top Product | 9 Column Feed |
|---|---|---|---|
| HF | 93.51 | 3.89 | 97.40 |
| FC-123 |  | 1.80 | 1.80 |
| FC-124 |  | 0.78 | 0.78 |
| Temp °C. | 132 | 97 | 0 |
| Press. MPa | 1.83 | 1.83 | 1.83 |

TABLE 8

| Compound | 11 Pure HF | 15 Top Product | 9 Column Feed |
|---|---|---|---|
| HF | 93.51 | 3.89 | 97.40 |
| FC-123 |  | 1.80 | 1.80 |
| FC-124 * |  | 0.78 | 0.78 |
| Temp °C. | 171 | 133 | 0 |
| Press. MPa | 3.55 | 3.55 | 3.55 |

EXAMPLE 4

If the purification system contains two multiple plate distillation columns (FIG. 2), then it is being operated under the conditions shown in Tables 9–14.

TABLE 9

| Compound | 1 Feed Mix. | 3 Decant Feed | 6 Acid Phase | 5 Organic Phase | 11 Pure HF | 15 Top Prod. | 21 Top Prod. |
|---|---|---|---|---|---|---|---|
| HF | 53.87 | 64.68 | 56.46 | 8.22 | 53.87 | 2.59 | 8.22 |
| FC-123 | 38.83 | 41.83 | 2.49 | 39.34 | 0.00 | 2.49 | 0.51 |
| FC-124 | 7.80 | 11.48 | 1.19 | 10.29 | 0.00 | 1.19 | 2.49 |
| Mole % HF |  |  | 93.9 | 14.2 |  |  |  |
| Temp °C. | 101 | 40 | 40 | 40 | 85 | 56 | 43 |
| Press. MPa | 1.83 | 1.83 | 1.83 | 1.83 | 0.69 | 0.69 | 0.69 |

TABLE 9-continued

| Compound | 9 Column Feed | 17 Organic Product |
|---|---|---|
| HF | 56.46 | 0.00 |
| FC-123 | 2.49 | 38.83 |
| FC-124 | 1.19 | 7.80 |
| Temp °C. | 70 | 83 |
| Press. MPa | 0.69 | 0.69 |

TABLE 10

| Compound | 1 Feed Mix. | 3 Decant Feed | 6 Acid Phase | 5 Organic Phase | 11 Pure HF | 15 Top Prod. | 21 Top Prod. |
|---|---|---|---|---|---|---|---|
| HF | 53.87 | 59.14 | 56.46 | 2.68 | 53.87 | 2.59 | 2.68 |
| FC-123 | 38.33 | 40.42 | 1.58 | 38.84 | 0.00 | 1.58 | 0.51 |
| FC-124 | 7.80 | 11.12 | 0.83 | 10.29 | 0.00 | 0.83 | 2.50 |
| Mole % HF | | | 95.9 | 5.1 | | | |
| Temp °C. | 101 | 0 | 0 | 0 | 85 | 56 | 43 |
| Press. MPa | 1.83 | 1.83 | 1.83 | 1.83 | 0.69 | 0.69 | 0.69 |

| Compound | 9 Column Feed | 17 Organic Product |
|---|---|---|
| HF | 56.46 | 0.00 |
| FC-123 | 1.58 | 38.33 |
| FC-124 | 0.83 | 7.78 |
| Temp °C. | 70 | 83 |
| Press. MPa | 0.69 | 0.69 |

TABLE 11

| Compound | 1 Feed Mix. | 3 Decant Feed | 6 Acid Phase | 5 Organic Phase | 11 Pure HF | 15 Top Prod. | 21 Top Prod. |
|---|---|---|---|---|---|---|---|
| HF | 53.87 | 57.29 | 56.47 | 0.82 | 53.88 | 2.59 | 0.82 |
| FC-123 | 38.33 | 39.86 | 1.02 | 38.84 | 0.00 | 1.02 | 0.51 |
| FC-124 | 7.80 | 10.90 | 0.57 | 10.32 | 0.00 | 0.57 | 2.51 |
| Mole % HF | | | 97.3 | 1.6 | | | |
| Temp °C. | 101 | −40 | −40 | −40 | 85 | 56 | 43 |
| Press. MPa | 1.83 | 1.83 | 1.83 | 1.83 | 0.69 | 0.69 | 0.69 |

| Compound | 9 Column Feed | 17 Organic Product |
|---|---|---|
| HF | 56.48 | 0.00 |
| FC-123 | 1.02 | 38.33 |
| FC-124 | 0.57 | 7.81 |
| Temp °C. | 70 | 83 |
| Press. MPa | 0.69 | 0.69 |

TABLE 12

| Compound | 1 Feed Mix. | 3 Decant Feed | 6 Acid Phase | 5 Organic Phase | 11 Pure HF | 15 Top Prod. | 21 Top Prod. |
|---|---|---|---|---|---|---|---|
| HF | 53.87 | 56.69 | 56.47 | 0.22 | 53.88 | 2.59 | 0.22 |
| FC-123 | 38.33 | 39.42 | 0.58 | 38.84 | 0.00 | 0.58 | 0.51 |
| FC-124 | 7.80 | 10.67 | 0.35 | 10.32 | 0.00 | 0.35 | 2.51 |
| Mole % HF | | | 98.4 | 0.4 | | | |
| Temp °C. | 101 | −80 | −80 | −80 | 85 | 56 | 43 |
| Press. MPa | 1.83 | 1.83 | 1.83 | 1.83 | 0.69 | 0.69 | 0.69 |

| Compound | 9 Column Feed | 17 Organic Product |
|---|---|---|
| HF | 56.47 | 0.00 |
| FC-123 | 0.58 | 38.33 |
| FC-124 | 0.35 | 7.81 |
| Temp °C. | 70 | 83 |
| Press. | | |

TABLE 12-continued

|  |  |  |
|---|---|---|
| MPa | 0.69 | 0.69 |

TABLE 13

| Compound | 1 Feed Mix. | 3 Decant Feed | 6 Acid Phase | 5 Organic Phase | 11 Pure HF | 15 Top Prod. | 21 Top Prod. |
|---|---|---|---|---|---|---|---|
| HF | 62.02 | 63.64 | 63.26 | 0.38 | 62.02 | 1.23 | 0.38 |
| FC-122 | 0.34 | 0.34 | t | 0.34 | 0.00 | t | t |
| FC-123 | 19.65 | 20.54 | 0.61 | 19.92 | 0.00 | 0.61 | 0.27 |
| TCE | 14.80 | 14.82 | 0.02 | 14.80 | 0.00 | 0.02 | t |
| FC-124 | 2.92 | 3.56 | 0.24 | 3.32 | 0.00 | 0.24 | 0.41 |
| Mole % HF |  |  | 98.6 | 1.0 |  |  |  |
| Temp °C. | 111 | −20 | −20 | −20 | 85 | 57 | 48 |
| Press. MPa | 1.83 | 1.83 | 1.83 | 1.83 | 0.69 | 0.69 | 0.69 |

| Compound | 9 Column Feed | 17 Organic Product |
|---|---|---|
| HF | 63.26 | 0.00 |
| FC-122 | t | 0.34 |
| FC-123 | 0.61 | 19.65 |
| TCE | 0.02 | 14.80 |
| FC-124 | 0.24 | 2.92 |
| Temp °C. | 70 | 104 |
| Press. MPa | 0.69 | 0.69 |

*Tetrachloroethylene
*Trace

TABLE 14

| Compound | 1 Feed Mix. | 3 Decant Feed | 6 Acid Phase | 5 Organic Phase | 11 Pure HF | 15 Top Prod. | 21 Top Prod. |
|---|---|---|---|---|---|---|---|
| HF | 128.96 | 152.09 | 141.16 | 10.94 | 128.96 | 12.20 | 10.94 |
| FC-123 | 69.44 | 84.95 | 6.57 | 78.39 | 0.00 | 6.57 | 8.95 |
| Mole % HF |  |  | 95.6 | 12.2 |  |  |  |
| Temp °C. | 101.40 | 40.00 | 40.00 | 40.00 | 85.38 | 64.05 | 64.09 |
| Press. MPa | 1.83 | 1.83 | 1.83 | 1.83 | 0.69 | 0.69 | 0.69 |

| Compound | 9 Column Feed | 17 Organic Product |
|---|---|---|
| HF | 141.16 | 0.00 |
| FC-123 | 6.57 | 69.44 |
| Temp °C. | 70.00 | 91.88 |
| Press. MPa | 0.69 | 0.69 |

What is claimed:

1. A Process for the separation of hydrogen fluoride from a mixture consisting essentially of hydrogen fluoride and at least one of 2,2-dichloro-1,1,1-trifluoroethane, and 2-chloro-1,1,1,2-tetrafluoroethane and minor amounts of halogenated materials consisting essentially of a combination of phase separation and distillation, said process comprising:

(a) condensing the mixture to a temperature from about −80° C. to about 40° C. and a pressure from about 0.10 MPa to about 3.55 MPa, in a separation zone so that an organic phase consisting essentially of at least 85 mole percent of at least one of 2,2-dichloro-1,1,1-trifluoroethane, and 2-chloro-1,1,1,2-tetrafluoroethane and less than 15 mole percent of HF is formed as the bottom layer in the separation zone and an acid phase consisting essentially of at least 93 mole percent of HF and less than 7 mole percent of at least one of 2,2,-dichloro-1,1,1-trifluoroethane, and 2-chloro-1,1,1,2-tetrafluoroethane is formed as the top layer in the separation zone, (b) removing the acid phase from the top of the separation zone, (c) feeding the acid phase from (b) to a distillation column at a temperature from about −4° C. to about 133° C. and a pressure from about 0.10 MPa to 3.55 MPa to form an azeotrope containing HF at the top of the distillation column and HF at the bottom of the distillation column, and (d) recovering the HF from the bottom of the distillation column.

2. The process of claim 1 wherein the azeotrope from step (c) is recycled to the separation zone.

3. A Process for the separation of hydrogen fluoride from a mixture consisting essentially of hydrogen fluoride and at least one of 2,2-dichloro-1,1,1-trifluoroethane, and 2-chloro-1,1,1,2-tetrafluoroethane and minor amounts of halogenated materials consisting essentially of a combination of phase separation and distillation, said process comprising:

(a) condensing the mixture to a temperature from about −80° C. to about 40° C. and a pressure from about 0.10 MPa to about 3.55 MPa, in a separation zone so that an organic phase consisting essentially of at least 85 mole percent of at least one of 2,2-dichloro-1,1,1-trifluoroethane, and 2-chloro-1,1,1,2-tetrafluoroethane and less than 15 mole percent of HF is formed as the bottom layer in the separation zone and an acid phase consisting essentially of at least 93 mole percent of HF and less than 7 mole percent of at least one of 2,2-dichloro-1,1,1-trifluoroethane, and 2-chloro-1,1,1,2-tetrafluoroethane is formed as the top layer in the separation zone, (b) removing the organic phase from the bottom of the separation zone, (c) feeding the organic phase from (b) to a distillation column at a temperature from about −15° C. to about 120° C., and a pressure from about 0.10 MPa to 3.55 MPa to form an azeotrope containing HF at the top of the distillation column and a mixture of at least one of 2,2-dichloro-1,1,1-trifluoroethane and 2-chloro-1,1,1,2-tetrafluoroethane at the bottom of the distillation column, and (d) recovering the mixture of (c) from the bottom of the distillation column.

4. The process of claim 3 wherein the azeotrope from step (c) is recycled to the separation zone.

5. A Process for the separation of hydrogen fluoride from a mixture consisting essentially of hydrogen fluoride and at least one of 2,2-dichloro-1,1,1-trifluoroethane, and 2-chloro-1,1,1,2-tetrafluoroethane and minor amounts of halogenated materials consisting essentially of a combination of phase separation and distillation, said process comprising:

(a) condensing the mixture to a temperature from about −80° C. to about 40° C. and a pressure from about 0.10 MPa to about 3.55 MPa, in a separation zone so that an organic phase consisting essentially of at least 85 mole percent of at least one of 2,2-dichloro-1,1,1-trifluoroethane, and 2-chloro-1,1,1,2-tetrafluoroethane and less than 15 mole percent of HF is formed as the bottom layer in the separation zone and an acid phase consisting essentially of at least 93 mole percent of HF and less than 7 mole percent of at least one of 2,2,-dichloro-1,1,1-trifluoroethane, and 2-chloro-1,1,1,2-tetrafluoroethane is formed as the top layer in the separation zone, (b) removing the acid phase from the top of the separation zone, (c) feeding the acid phase from (b) to a distillation column at a temperature from about −4° C. to about 133° C. and a pressure from about 0.10 MPa to 3.55 MPa to form an azeotrope containing HF at the top of the distillation column and HF at the bottom of the distillation column, and (d) recovering the HF from the bottom of the distillation column, (e) removing the organic phase from the bottom of the separation zone, (f) feeding the organic phase from (e) to a distillation column at a temperature from about −15° C. to about 120° C. and a pressure from about 0.10 MPa to 3.55 MPa to form an azeotrope containing HF at the top of the distillation column and a mixture of at least one of 2,2-dichloro-1,1,1-trifluoroethane and 2-chloro-1,1,1,2-tetrafluoroethane at the bottom of the distillation column and (g) recoving the mixture of (f) from the bottom of the distillation column.

6. The process of claim 5 wherein the azeotropes from steps (c) and (f) are recycled to the separation zone.

* * * * *